United States Patent [19]  [11] 4,138,479
Truscheit et al.  [45] Feb. 6, 1979

[54] PROCESS FOR THE PREPARATION OF IMMUNOPOTENTIATING AGENTS FROM COMPONENTS OF YEAST CELL WALL MATERIAL

[75] Inventors: Ernst Truscheit, Doenberg; Robert Bierling; Horst D. Schlumberger, both of Wuppertal, all of Fed. Rep. of Germany; Herbert F. Oettgen, New York, N.Y.

[73] Assignee: Bayer Aktiengesellschaft, Fed. Rep. of Germany

[21] Appl. No.: 832,300

[22] Filed: Sep. 12, 1977

Related U.S. Application Data

[63] Continuation-in-part of Ser. No. 629,927, Nov. 7, 1975, abandoned.

[51] Int. Cl.² ............... A61K 39/00; A61K 39/02; A61K 31/70
[52] U.S. Cl. ................................. 424/88; 424/92; 424/180; 424/195
[58] Field of Search .................. 424/88, 92, 180

[56] References Cited

U.S. PATENT DOCUMENTS 3,081,226  3/1963  DiLuzio .................... 424/180
3,148,120  9/1964  Westphal .................. 424/92

FOREIGN PATENT DOCUMENTS 2452303  5/1976  Fed. Rep. of Germany.
2981M    2/1963  France.

OTHER PUBLICATIONS

Fitzpatrick et al., Annals of N.Y. Academy of Sci., vol. 118, Art 4, pp. 235 to 261 (Oct. 15, 1964).
Allen, "Ribonucleoproteins and Ribonucleic Acids" Elsevier Publishing Co. N.Y. (1962, pp. 104–107, 160–171.

Primary Examiner—Donald B. Moyer
Attorney, Agent, or Firm—Jacobs & Jacobs

[57] ABSTRACT

A water soluble immunopotentiating agent is derived from yeast cell wall material, including mechanically disrupted yeast cell walls, proteolyzed yeast cell wall material and carbohydrate-protein complexes found in yeast cell wall material, through extraction with a water-phenol mixture. The water soluble agent is isolated from the water phase and can be further purified, as through dialysis, to remover low molecular weight components.

11 Claims, No Drawings

PROCESS FOR THE PREPARATION OF IMMUNOPOTENTIATING AGENTS FROM COMPONENTS OF YEAST CELL WALL MATERIAL

CROSS-REFERENCE

This application is a continuation-in-part of application Ser. No. 629,927, filed Nov. 7, 1975, now abandoned.

DETAILED DESCRIPTION

The present invention relates to new immunopotentiating agents extracted from yeast cell wall materials and to processes for their preparation.

It is known that the water-insoluble residue obtained upon autolysis or proteolysis, as for example treatment with trypsin, of baker's yeast stimulates the immunological defense mechanism. This has been demonstrated through observation of growth-inhibiting action on certain neoplasms. This material, a modified yeast cell wall material about which little chemical information has been elucidated but which may be polypeptide in nature, has been labelled "zymosan" and is described by J. Nagy et al., Archivo Italiano di Patologia e Clinica dei Tumori Vol. XIV, Fasc. 3-4-1971, pages 29–35 and F. W. Fitzpatrick and F. I. Di Carlo: Zymosan, Ann. New York Acad. Sci. 118 (4), 233-262 (1964).

It has now been found that new extraction products which are complex polysaccharides and significantly water soluble can be obtained from material containing yeast cell wall constituents. These materials have been shown to have strong immunopotentiating activity, especially acceleration of phagocytosis and inhibition of the growth of neoplasma. This activity is considerably greater than that which has been demonstrated for zymosan.

The starting material used in this process include proteolytic degradation products of yeast cells as for example those obtained upon treatment with trypsin or through autolytic degradation of yeast cell wall constituents (these being the so-called zymosans), and the polysaccharide-protein complexes of yeast cell walls, for example glucomannan-protein complex or glucan-protein complex.

Since the material appears to be characteristic of yeast cell wall material in general and not limited to a single species, substantially any and all species of yeast can be used. For example, it is possible to use commercially available baker's yeast (as well as special strains of yeast which are either commercially available for can be isolated as single strains from commercially available yeast, and cultured). These include Saccharomycetaceae (sub-families: Saccharomycetoideae, Schizosaccharomycetoideae, Eramascoideae, Endomycetoideae, Lipomycetoideae and Namatosporoideae; Sporobolomycetaceae; and Cryptococcaceae (sub-families: Cryptococcoideae, Trichosporoideae and Rhodotoruloideae). Other suitable strains are classified by J. Lodder et al. in A. H. Cook (Ed), *The Chemistry and Biology of Yeasts*, Academic Press New York 1958, page 1 et seq. and P. A. J. Gorin and J. E. T. Spencer in D. Perlman (Ed.) *Advances in Applied Microbiology;* Vol 13, Academic Press New York, 1970, page 25 et seq. Genera of the sub-family Saccharomycetoideae, belonging to the Saccharomyceteae, and of the sub-family Cryptococcoideae have proved very effective. Thus one can employ a Saccharomyces, such as *saccharomyces cerevisiae* strains, a Candida, such as *Candida utilis* or Kloeckera.

The present invention thus pertains to a process for the preparation of a water soluble immunopotentiating agent from components of yeast cell walls which comprises subjecting yeast cell wall material, proteolyzed yeast cell wall material or a carbohydrate-protein yeast cell wall material to extraction with water and phenol and thereafter isolating the water soluble agent. The phenol-water extraction which is used is somewhat similarly described by O. Westphal et al., Z. Naturforsch 7b, 148 (1952), with a number of modifications.

In general, the yeast cell starting material is heated with a 10 to 100-fold, preferably 30 to 40-fold, amount of a mixture of substantially equal parts by volume of phenol and water. This is conducted for a short time, preferably for about 10 to about 30 minutes at temperatures of between about 40 and about 100° C., preferably 55 to 75° C. This is then centrifuged at temperatures between from about 0 and about 35° C. One advantageous procedure which can be followed is to first suspend the yeast starting material in a 5 to 50-fold, preferably 15 to 20-fold, amount of water and then to stir the suspension with approximately an equal volume of phenol such as 90% strength, and after heating to 68° C., for about 15 minutes at this temperature. Upon centrifugation, the phenol and solid phases, of which there may be three, are combined and again heated for a short period with further volume of water. After further centrifugation, the aqueous phases are combined.

In the phenol-water treatment of the yeast cell constituents, as for example zymosan and yeast, separation into three phases generally occurs upon centrifugation, namely an aqueous phase, a solid phase and a phenolic phase. With zymosan, the solid phase is between the two liquid phases, while with yeast, the solid constituents are found in the upper and lower part of the phenol phase. In general, the solid phases produced will in either event contain phenol and they are thus an integral, although separable, constituent of the phenol phase.

The nature of a typical phenol-water extraction, and subsequent processing can be diagrammatically depicted as follows.

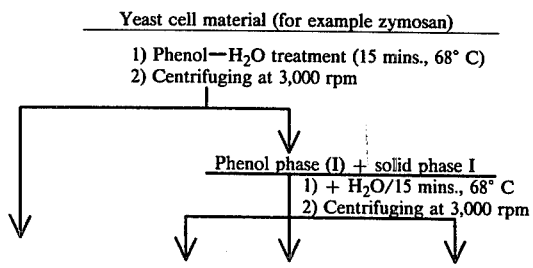

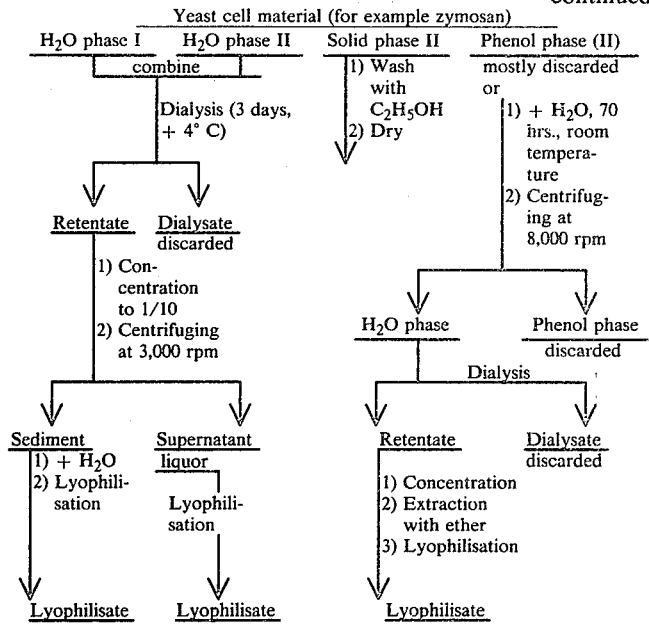

As is apparent from the foregoing flow scheme, the water soluble material in the aqueous phases can be further purified in each case, as for example by dialysis. This is carried out for several days, e.g. 2 to 5 days, at temperatures between 0° and 50° C., preferably at 3° to 35° C., and the retentate is then processed further as desired. For example the retentate from the dialysis is concentrated to 5–20, preferably 8–15, percent of its original volume and is then centrifuged, whereupon a sediment and a supernatant liquor are produced. Both are then lyophilized, the sediment in each case being taken up in water before lyophilization.

In addition to the purification scheme depicted above, other methods can be used. For example, undesired low molecular constituents can be separated from the aqueous phases by gel filtration, ultrafiltration or by a combination of some or all of the above mentioned methods, including dialysis.

Should it prove difficult to separate the phenol completely from the aqueous phase, the former can be extracted from the latter, as for example after dialysis or gel filtration, through the use of an organic solvent for phenol such as ether or chloroform which is not miscible with water.

The immunopotentiating properties of these agents can be conveniently observed in recognized laboratory models such as stimulation of the reticulo endothelial system and the tumorimmuno-screening assays. In the latter model, $1 \times 10^6$ ascites cells of sarcoma 180, in 0.5 ml of 0.9% NaCl solution, are inoculated, intraperitoneally, into colony bred Swiss mice weighing 20 to 22 g for maintenance of the strain, 7 days after the last transplant of the tumor. Screening tests are conducted in the same fashion, but $5 \times 10^5$ tumor ascites cells in 0.3 ml of solution are used for subcutaneous inoculation. Assay of the immunopotentiating agent are conducted with the aqueous preparation solutions or suspensions by a single intraperitoneal, subcutaneous, intramuscular or intravenous injection on either the 7th day prior to or on the 7th day after the tumor transplant. The experiments in each case lasts 28 days, after which the animals are sacrificed and examined. The death of animals is recorded and the general condition of the animals is assessed, as are the changes in body weight, the change in the leucocyte count in the peripheral blood and the macroscopic changes of the organs. The evaluation parameter used in the inhibition of tumor growth which is determined quantitatively by determining the tumor weight index (TW index) as follows:

$$\text{TW index} = \frac{\text{average tumor weight of the treated animals}}{\text{average tumor weight of the untreated control}}$$

The evaluation of the TW index values is as follows:
TW index 1.0–0.8 = no effect
0.7–0.6 = slight effect
0.5–0.4 = significant effect
0.3–0.2 = good effect
0.1–0.0 = very good effect

| Substance | Optimum effective dose mg/kg, 1 × i.p. | Day of administration | Tumor weight index | Animals dead/employed |
|---|---|---|---|---|
| Zymosan Example 1A | 20 | −7 | 0.5 | 0/6 |
|  | 20 | +7 | 0.5 | 0/6 |
| Phenol-water extract of zymosan Example 1A(2) (a) | 200 | −7 | 0.02 | 0/6 |
|  | 100 | +7 | 0.1 | 0/6 |
| Yeast cell wall material Example 1B(1) | 100 | −7 | 0.9 | 0/8 |
|  | 100 | +7 | 0.7 | 1/8 |
| Phenol-water extract of yeast cell walls - Example 1B(2) (a) | 100 | −7 | 0.3 | 0/10 |
|  | 100 | +7 | 0.4 | 0/10 |

$$\text{TW index} = \frac{\text{average tumor weight of the treated animals}}{\text{average tumor weight of the untreated control}}$$

The evaluation of the TW index values is as follows:
TW index 1.0–0.8 = no effect
0.7–0.6 = slight effect
0.5–0.4 = significant effect
0.3–0.2 = good effect
0.1–0.0 = very good effect

| Substance | Optimum effective dose mg/kg, 1 × i.p. | Day of administration | Tumor weight index | Animals dead/employed |
|---|---|---|---|---|
| Yeast cell wall zymosan | 250 | −7 | 1.1 | 0/10 |
| Example 1B(3) | 250 | +7 | 1.3 | 0/10 |
| Phenol-water extract of yeast cell wall zymosan - Example 1B(4)(a) | 50 | −7 | 0.3 | 0/10 |
| | 50 | +7 | 0.1 | 0/8 |
| Glucan-protein complex | 250 | −7 | 0.5 | 0/10 |
| Example 1B(5)(c) | 250 | +7 | 0.4 | 0/10 |
| Phenol-water extract of glucan-protein complex - Example 1B(5)(c)(i) | 250 | −7 | 0.2 | 1/10 |
| | 250 | +7 | 0.2 | 0/10 |

The carbon clearance test can be used to observe the stimulating of the reticulo endothelial system (RES). This stimulation of phagocytic activity is an aspect of immunopotentiation in addition to tumor inhibition. The test substance is injected intramuscularly into female $CF_1$-mice weighing 20 to 22 g. To assess the activity of the reticulo-endothelial system (RES) groups of 5 animals are injected intravenously with 16 mg/100 g of body weight of carbon particles (200 to 500%) in a total volume of 0.2–0.3 ml on the 1st, 2and, 3rd, 6th, 8th, 10th, 13th and 15th days after the initial injection. The clearance of the carbon particles from the blood stream is determined by bleeding the animals from the retroorbital sinus 3, 6, 10, 15, 20 and 30 minutes after injection of carbon and the content of carbon particles in the blood is determined photometrically, the concentration of carbon in the samples being quantified by a calibration curve. From these data, the clearance constant K can be calculated according to the following formula:

$$K = \frac{\ln C_o - \ln C_t}{t}$$

where $\ln C_o$ is the natural logarithm of the concentration of carbon particles at time 0, $\ln C_t$ is the natural logarithm of the concentration of carbon particles at time t. $C_o$ is determined by graphical extrapolation. The constant K expresses the velocity of the disappearance of carbon particles from the blood stream which are phagocytosed and stored in cells of the reticulo-endothelial system.

The normal range of K in female $CF_1$-mice is 0.02 ± 0.0045. Values above the upper limit indicate an enhanced activity of the RES, i.e., accelerated phagocytosis of the carbon particles. The RES is part of the immune system in that particulate and/or immunogenic material is phagocytosed, concentrated and processed by cells of the RES for further handling by immunocompetent cells.

Utilizing the water soluble material of Example 1A(2)(a), the following data are observed in the carbon clearance test.

| | Day After Administration | | | | | | | |
|---|---|---|---|---|---|---|---|---|
| | 1 | 2 | 3 | 6 | 8 | 10 | 13 | 15 |
| K | .0330 | .0437 | .0642 | .0340 | .0465 | .0498 | .0493 | .0469 |
| spleen weight mg | 94 | 87 | 105 | 97 | 100 | 91 | 98 | 111 |

The normal range of the spleen weight in female $CF_1$-mice is 94 ± 16 mg and the spleen weight of the treated animals remains within this normal range during the 15 days of observation. This indicates that the effect of the substance is due to an increase of the functional activity of specific cells of the RES.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The material of the present invention potentiates the immunological response in an animal or human through administration to the animal or human of an immunologically potentiating amount of the material. Generally, such a response can be observed upon administration of from about 10 to about 50 mg/kg of body weight of the purified agent per day. Although any of the usual pharmaceutical modes of administration can be employed, it is preferable to utilize the parenteral routes such as intramuscular, intraperitoneal, intravenous or subcutaneous injection. It is to be appreciated that in view of the nature of the condition being treated, the dose must, in each case, be titrated to the patient, taking into consideration the general condition, age, weight and response desired. In each instance, administration should only be effected utilizing sound professional judgement. It will further be appreciated that the properties of these agents is one of potentiating the animals own immunological defense mechanism and thus all immunological parameters should be monitored during and after administration. The present disclosure is specifically directed at the medical and veterinarian arts, and the allied arts, and should not be construed as a suggestion or recommendation for use by others in the absence of such professional guidance and without compliance with all applicable Federal and state laws.

The following examples will serve to typify the process of the present inventions and the products thereby formed, together with a number of comparative products. These examples should not be construed as a limitation on the scope of the present invention, the invention being defined solely by the appended claims.

EXAMPLE 1

A. Zymosan and zymosan fractions from *Saccharomyces cerevisiae*

(1) Preparation of Zymosan (in a modified form, according to PILLEMER et al., I. exp. Med. 103, 1-13 (1956)).

Yeast (*Saccharomyces cerevisiae* spec., an isolated strain from commercially available baker's yeast) is cultured under sterile conditions on a 2,000 liter scale, and 12 kg of the sediment of pasty consistency, obtained after centrifuging the culture, are mixed, in a 50 liter round flask surmounted by a stirrer and fitted with a filling tube, with 48 liters of 0.5 M disodium hydrogen phosphate buffer (pH 8.9). The completely closed apparatus is now heated to 100° C. in an autoclave for 4 hours, to effect sterilisation. After slowly being allowed to cool to +37° C., about 500 ml of toluene are added, followed by a sterile-filtered solution of 5 g of trypsin in 50 ml of phosphate-buffered 0.9% strength sodium chloride solution (pH 7.2). The reaction time is in total 16 days at 37° C. (thermostatically controlled water bath; circulating pump). The contents of the flasks are stirred thoroughly for about 30 minutes each day. A sample is then withdrawn under sterile conditions in order to determine the pH. If required — and experience shows that this is only necessary very rarely — the pH value of the reaction mixture is adjusted to pH 8.0–8.2 by adding concentrated sodium hydroxide solution. On the 3rd, 6th and 10th day, the sterile-filtered trypsin solution already described (5 g/50 ml) is added in each case.

Similar results are obtained on using substantially shorter proteolysis times, for example of 4 days (addition of 5 g of trypsin/50 ml of NaCl solution on the 1st day and again on the 3rd day in the case of a batch of 12 kg of yeast paste) or of 6 days (addition of 5 g of trypsin/50 ml of NaCl solution on the 1st day, again on the 3rd day, and again on the 5th day, in the case of a batch of 12 kg of yeast paste).

The next working-up step takes about 2 days. First, the contents of the flask are centrifuged at 19,000 revolutions per minute, using a flow-through centrifuge. The sediment is vigorously stirred in about 50 liters of cold (about 12° C.) tap water, to which about 20 ml of toluene have been added, for 1 hour. The suspension is again centrifuged as indicated above and the sediment is again suspended in about 50 liters of cold tap water; the suspension is heated to 90° C. for about 1 hour, with vigorous stirring. The mixture is cooled to room temperature and again centrifuged as indicated above. This process is repeated with the sediment obtained, and the sediment thus obtained is suspended in about 50 liters of distilled water, to which about 20 ml of toluene have been added; the suspension is left at +4° C. overnight. The mixture is then heated for 1 hour to 90° C., while stirring, cooled to room temperature and centrifuged in the same manner as already described. The sediment is stirred vigorously for 1 hour at room temperature in about 80 liters of denatured ethanol (so-called "dry-spirit," about 99.8% strength). The suspension is filtered and the filter cake is again stirred vigorously for 1 hour in 40 liters of denatured ethanol (see above). This suspension is filtered and the filter cake is washed on the filter with about 5 liters of ethanol (see above). Thereafter the filter cake is dried on a drying tray in a vacuum drying cabinet at room temperature for 24 hours. The dried product is suspended in 6 liters of ethanol (see above) and the suspension is refluxed for 3 hours, while stirring. The mixture is then cooled to room temperature and filtered. The filter cake is washed on the filter with ethanol and again dried for 24 hours in a vacuum drying cabinet at room temperature.

The yield is 450–500 g of zymosan (= about 4%, or 14–15% relative to lyophilised yeast).

(2) Phenol-water extracts (a) Supernatant liquor from the retentate obtained after dialysis of the aqueous phase 200 g of zymosan are suspended in 3.5 liters of distilled water at room temperature; thereafter, 3.5 liters of 90% strength phenol are added while stirring and the mixture is then heated to 68° C. for 15 minutes, while stirring. After cooling to +15° C., the emulsion thus obtained is centrifuged at 3,000 revolutions per minute and +10 ° C. 3 phases are obtained;

an aqueous phase (upper phase)

a solid phase (middle phase: zymosan residue + phenol + water)

a liquid phenolic phase (lower phase).

The aqueous phase is carefully siphoned off. The two remaining phases are heated with 3.5 liters of distilled water to 68° C. for 15 minutes, while stirring. After cooling to +15° C., the process described above is repeated. Three phases are again formed. The aqueous phase thus obtained, combined with the aqueous phase first isolated (see above), is dialysed against distilled water for three days at 4° C. The retentate is concentrated in a rotary evaporator under reduced pressure at 35°–40° C. to 1/10 of its initial volume, whereby a precipitate is formed, which is centrifuged off at +10° C. (3,000 revolutions per minute). The supernatant liquor is lyophilised. Yield: 7–8 g of the phenol-waterextract.

In order to accomplish a complete separation of phenol the above mentioned retentate after its concentration in a rotary evaporator is shaken with about one half of its final volume of diethylether. The aqueous phase is separated in a separation funnel and shaken again with about one half of its volume of diethylether. After separation of the aqueous phase a third ether extraction is performed in the same manner. Finally, the aqueous phase is lightly swirled in a round flask under reduced pressure to remove the ether, and is then centrifuged in order to separate the above mentioned precipitate which mostly exists in a highly dispersed form.

(b) Precipitate from the retentate obtained after dialysis of the aqueous phase

The sediment described above is taken up in about 100 ml of distilled water and the suspension thus obtained is lyophilised.

Yield: 4–6 of the phenol-water extract.

(c) Solid phase, washed

After siphoning off the aqueous phase obtained in A(2) (a), the solid phase which rests on the phenol phase is pierced with an inverted pipette and the phenol phase below it is carefully sucked off. Thereafter, the solid phase is suspended in 6–8 liters of denatured ethanol (see above) and the suspenson is stirred for 1 hour at room temperature. After filtering off (on a normal filter) the filter cake is washed twice with 3 liters of ethanol (see above) at a time. The thoroughly suction-drained filter cake is dried for 24 hours in a vacuum drying cabinet at 50° C.

Yield: about 180 g.

The residue thus obtained can, like zymosan, be subjected to a further phenol-water treatment. This gives about 2 g of residue from the retentate obtained after dialysis of the aqueous phase and about 1 g of precipitate from the above mentioned retentate.

A further phenol-water extraction of the solid phase obtained in this process step and worked up as described above gives about 500 mg of supernatant liquor or 200 mg of precipitate.

(d) Phenol phase, worked up

The phenol phase obtained in A(2) (a) is stirred with 3 liters of distilled water for about 70 hours at room temperature and the resulting emulsion is centrifuged for 20 minutes at 8,000 revolutions per minute and +4° C. The phenolic lower phase is discarded and the aqueous phase is dialysed at +4° C. for three days against distilled water. The retentate is concentrated in a rotary evaporator under reduced pressure at about 40° C. to approximately 1/10 of the initial volume and after cooling, the concentrate is extracted by shaking with five times 500 ml of ether. The aqueous phase is lightly swirled in a round flask under reduced pressure to remove the ether, and is then lyophilised. About 250 mg of a hygroscopic residue are obtained.

B. Yeast cell wall preparations from *Saccharomyces cerevisiae*

(1) Yeast cell walls

The moist yeast mass (cultured under sterile conditions of pasty consistency, described above, is lyophilised, as a result of which about 270 g of dry mass are obtained from 1 kg.

200 g of the lyophilisate are stirred with 600 ml of 0.9% strength sodium chloride solution to give a pasty mass and are disintegrated for 2 hours with 970 g of glass beads (0.4–0.5 mm diameter) in a so-called "pigment mill" at +4° C. The homogenised material, free from glass beads, is run off and the glass beads which have remained in the mill are washed with 1 liter of 0.9% strength sodium chloride solution. The homogenised material and the sodium chloride wash solution are combined. The suspension thus obtained is centrifuged in the flow-through rotor of a refrigerated centrifuge at 12,000 revolutions per minute and +4° C. The sediment from six such batches, which have been stored deep-frozen (−20° C.) (totalling 1.2 kg) is suspended in 20 liters of 0.2% strength sodium chloride solution and the suspension is stirred for 1 hour at room temperature. The cell walls are centrifuged off as described above and re-suspended in 20 liters of 0.9% strength sodium chloride solution. After stirring for one hour at room temperature, the suspension is again centrifuged as described above and the sediment is stirred in 10 liters of distilled water for 1 hour at room temperature. The cell walls are now centrifuged off for the last time as described above and stirred in 5 liters of denatured ethanol (see above) for 1 hour at room temperature, and then filtered off. The filter cake is washed on the filter with about 5 liters of denatured ethanol and dried in a vacuum drying cabinet at 50° C. for 24 hours.

Yield: 254 g of yeast cell wall preparation (= about 21%, relative to lyophilised yeast, or = 6%, relative to moist yeast mass).

(2) Phenol-water extracts from yeast cell walls (a) Supernatant liquor from the retentate obtained after dialysis of the aqueous phase 200 g of yeast cell walls obtained from yeast cultured under sterile conditions are treated with phenol-water as indicated in A(2) (a), and worked up.

Yield: about 10 g of phenol-water extract.

(b) Precipitate from the retentate obtained after dialysis of the aqueous phase

The procedure followed is the same as in A(2) (a) and A(2) (b).

Yield: 3–6 g of the phenol-water extract.

(3) Yeast cell wall zymosan 694 g of cell walls from yeast cultured under sterile conditions (corresponding to 12 kg of moist yeast) are reacted with trypsin for 16 days, in the same manner as indicated in A(1). After centrifuging the contents of the flask [flow-through centrifuge, see A(1)], the sediment is vigorously stirred for 1 hour in about 20 liters of cold distilled water. The suspension is now centrifuged in a cup centrifuge for 30 minutes at 3,000 revolutions per minute and the sediment is washed three times with distilled water, in the same manner as has been described. The sediment is then suspended in 20 liters of ethanol and the suspension is stirred for 1 hour at room temperature. After filtration, the filter cake is dried for 24 hours in a vacuum drying cabinet at 50° C. The dried product is suspended in 6 liters of ethanol and the suspension is then refluxed for 3 hours while stirring. The mixture is cooled to room temperature and the filter cake is washed on the filter with ethanol and again dried for 24 hours in a vacuum drying cabinet. The yield is 258 g (about 37%).

(4) Phenol-water extracts from yeast cell wall zymosan (a) Supernatant liquor from the retentate obtained after dialysis of the aqueous phase 200 g of yeast cell wall zymosan are treated with phenol-water, and worked up, as indicated in A(2) (a).

Yield: 500 mg of phenol-water extract.

(b) Precipitate from the retentate obtained after dialysis of the aqueous phase

Working up takes place as indicated in A(2) (b).

Yield: 4.9 g of phenol-water extract.

(c) Solid phase, washed

Working up takes place as indicated in A(2) (c).

Yield: 184.5 g.

(5) Polysaccharide-protein complexes from yeast cell walls

A glucomannan protein was prepared from yeast cell walls (from yeast which had been fermented under sterile conditions) by the method of KESSLER and NICKERSON [G. Kessler and W. J. Nickerson, J. biol. Chem. 234, 2,281–2,285 (1959)]. The preparations were furthermore subjected to a phenol-water extraction.

(a) Preparation of Glucomannan protein I 20 g of yeast cell wall preparation are freed from lipids, in the manner described by Kessler and Nickerson [G. Kessler and W. J. Nickerson, J. biol. Chem. 234, 2,281–2,285 (1959)] by treatment with alcohol + ether and subsequently with chloroform, and are then extracted with 1 N potassium hydroxide solution. Precipitation with ammonium sulphate gives, after dialysis and freeze-drying, 6.5 g glucomannan protein I.

Phenol-water extracts (i) Supernatant liquor from the retentate 50 g of glucomannan protein I are suspended in 850 ml of distilled water as indicated in A(2) (a) and after addition of 850 ml of phenol the suspension is heated to 68° C. for 15 minutes. Three phases are obtained, in the same manner as in A(2) (a). The re-extraction of the solid phase and of the phenol phase is carried out with 850 ml of distilled water.

Yield: 2.8 g of phenol-water extract.

(ii) Precipitate from the retentate

The precipitate obtained on concentrating the retentate obtained in B(5) (a) (i) is centrifuged off in the usual manner and the sediment is taken up in about 100 ml of distilled water and lyophilised.

Yield: 4.8 g of phenol-water extract.

(iii) Solid phase, washed

The solid phase obtained from the phenol-water treatment is suspended in 3 liters of denatured ethanol in the same manner as that indicated under A(2) (c) and after stirring the suspension for one hour the product is filtered off at room temperature. The filter cake is washed with twice 500 ml of ethanol and dried in a desiccator at room temperature over phosphorus pentoxide.

Yield: 24.9 g.

(b) Preparation of Glucomannan protein II

The supernatant liquor obtained when preparing glucomannan protein I is dialysed, concentrated and lyophilised, as indicated by Kessler and Nickerson [G. Kessler and W. J. Nickerson, J. biol. Chem. 234, 2,281–2,285 (1959)].

Yield: 2–3 g of glucomannan protein II.

Phenol-water extracts (i) 18.6 g of glucomannan protein II are suspended in 347 ml of distilled water as indicated in A(2) (a). After adding 347 ml of phenol, the suspension is heated to 68° C. for 15 minutes. Three phases are obtained, as indicated in A(2) (a), but are more difficult to separate. The emulsion is therefore centrifuged for 1 hour at 12,000 revolutions per minute and +10° C. Once again, the solid phase and the phenol phase are combined and re-extracted with 347 ml of water. The separation of the phases is carried out as described above. The aqueous phases obtained from the two process steps are combined and dialysed for three days against distilled water at +4° C.

Yield: 9.5 g of phenol-water extract.

(ii) Precipitate from the retentate

The precipitate obtained on concentrating the retentate obtained in B(5) (b) (i) is centrifuged in the usual manner and the sediment is taken up in about 100 ml of distilled water and lyophilised.

Yield: 1.8 g of phenol-water extract.

(iii) Solid phase

Since only very small amounts of a relatively smeary solid phase are obtained, the latter is discarded.

(c) Preparation of Glucan protein

The residue obtained from the preparation of the glucomannan proteins I + II is washed with distilled water until neutral, then treated with denatured ethanol, and dried in vacuo.

Yield: 4.5 g of glucan protein.

Phenol-water extracts (i) Supernatant liquor from the retentate 30 g of glucan protein are suspended in 500 ml of distilled water is indicated in A(2) (a). After adding 500 ml of phenol the suspension is heated to 68° C. for 15 minutes. Further working up takes place as indicated in A(2) (a).

Yield: 2.8 g of phenol-water extract.

(ii) Precipitate from the retentate

The precipitate obtained on concentrating the retentate obtained in B(5) (c) (i) is worked up in the usual manner.

Yield: 2.2 g of phenol-water extract.

(iii) Solid phase, washed

The solid phase is worked up in the same manner as indicated in B(5) (a) (iii) (glucomannan protein I).

Yield: 18.2 g.

EXAMPLE 2

Zymosan and zymosan fractions from *Candida utilis*

A. Preparation of Zymosan

Similarly to the description of Example 1 A(1), 4.8 liters of 0.5 M disodium hydrogen phosphate buffer (pH 8.5) are added to 200 g of dry yeast (*Candida utilis*, dried at a low temperature). After heating the closed apparatus in an autoclave (4 hours at 100° C.), the contents of the flask are allowed to cool slowly to +37° C., and about 500 ml of toluene are added, followed by 0.5 g of trypsin in 5 ml of phosphate-buffered 0.9% strength sodium chloride solution (pH 7.2). The reaction time totals 4 days at 37° C. (incubation chamber; the contents of the flask are stirred from time to time). 2 Days after the start of the enzymatic reaction (trypsin) a sterile-filtered trypsin solution (0.5 g/5 ml; see above) is again added. The pH value of the contents of the flask is checked daily. If necessary, the pH value of the reaction mixture is adjusted to pH 8.0–8.2 by adding concentrated sodium hydroxide solution.

Working up takes place as indicated in Example 1 A(1) except that, firstly, the reaction was discontinued after only 4 days and, secondly, about 1/10 of the amounts of solvent (water or ethanol) indicated in Example 1 was used. Furthermore, correspondingly less toluene was also employed.

Yield: 60 g.

B. Phenol-water extracts from zymosan according to Example 2 A (1) Supernatant liquor from the retentate obtained after dialysis of the aqueous phase 50 g of *Candida utilis* zymosan are treated with 875 ml of water and 875 ml of 90% strength phenol and worked up analogously to the procedure of Example 1.

Yield: 0.5 g of phenol-water extract (supernatant liquid from the retentate).

(2) Precipitate from the retentate obtained after dialysis of the aqueous phase

The precipitate obtained from working up as described under Example 2 B(1) is taken up in about 100 ml of distilled water and the suspension thus obtained is lyophilised.

Yield: 0.4 g of the phenol-water extract (precipitate from the retentate).

(3) Solid phase, washed

The solid phase obtained from the phenol-water extraction is worked up analogously to the instructions in Example 1 A(1) (c).

Yield: 43 g.

Analytical data of phenol-water extraction products according to the invention:

| Example No. | C | H | N |
|---|---|---|---|
| 1 A(2)(a) | 48.6% | 7.6% | 1.3% |
| 1 B(2)(a) | 44.9% | 6.7% | 4.4% |
| 1 B(2)(b) | 44.3% | 6.3% | 3.7% |
| 1 B(4)(a) | 41.2% | 6.4% | 1.0% |
| 1 B(4)(b) | 44.7% | 6.9% | 0.6% |
| 1 B(5)(a)(i) | 35.3% | 5.9% | 3.4% |
| 1 B(5)(a)(ii) | 38.6% | 6.3% | 1.2% |

The following sugars were detected in the acid hydrolysate of phenol-water extraction products according to the invention:

| Example No. | Glucose | Mannose | Xylose |
|---|---|---|---|
| 1 A(2)(a) | + | + | − |
| B(2)(a) | + | + | − |
| B(2)(b) | + | + | − |
| B(4)(a) | + | + (little) | − |
| B(4)(b) | + | + (little) | − |
| B(5)(b)(i) | + | + | + |
| B(5)(b)(ii) | + | + | + |
| B(5)(c)(i) | + | + | − |
| B(5)(c)(ii) | + | + | − |

From the low nitrogen content, generally less than 5%, and the characteristic water solubility, the material is clearly not proteinaceous. The presence of at least glucose and mannose upon acid hydrolysis indicate the material is a complex polysaccharide which is also in agreement with the observed water solubility.

The material is also distinct from glucan, as is apparent from comparison of the effects on sarcoma 180 in vivo of water soluble fraction of Ex. 1A. (2) (a) and glucan.

| | Dose mg/kg 1 × o.p | No. of mice tumor regression total |
|---|---|---|
| water soluble material of Example 1A.(2)(a) | 20 | 3/ 9 |
| | 80 | 5/10 |
| | 320 | 8/10 |
| Glucan | 20 | 3/10 |
| | 80 | 2/10 |
| | 320 | 4/10 |

What is claimed is:

1. The process for the preparation of a water soluble immunopotentiating agent from components of yeast cell walls which comprises subjecting yeast cell wall material, proteolyzed yeast cell wall material or a carbohydrate-protein yeast cell wall material to extraction with water and phenol and thereafter isolating the water soluble agent.

2. The process according to claim 1 wherein any low molecular weight sugars, amino acids, peptides, lipids and yeast metabolites are removed from said aqueous phase by subjecting the same to gel filtration, ultrafiltration or dialysis prior to isolating said immunopotentiating agent.

3. The process according to claim 2 wherein said low molecular weight sugars, amino acids, peptides, lipids and yeast metabolites are removed by dialysis, said immunopotentiating material being obtained from the dialysis retentate.

4. The process according to claim 1 wherein said extraction is effected with a mixture of substantially equal parts of water and phenol.

5. The process according to claim 4 wherein the amount of said mixture is from about 10 to about 100 times the weight of the material being extracted.

6. The process according to claim 1 wherein mechanically disrupted yeast cell wall material is subjected to extraction with from 10 to 100 times the amount by volume of a mixture of substantially equal amounts of water and phenol, and the aqueous phase is separated and thereafter dialyzed to remove any low molecular weight sugars, amino acids, peptides, lipids and yeast metabolites, said immunopotentiating agent being isolated from the dialysis retentate.

7. The water soluble immunopotentiating agent produced according to the process of claim 6.

8. The process according to claim 1 wherein trypsin-proteolyzed yeast cell wall material is subjected to extraction with from 10 to 100 times the amount by volume of a mixture of substantially equal amounts by volume of water and phenol and the aqueous phase is separated and thereafter dialyzed to remove any low molecular weight sugars, amino acids, peptides, lipids and yeast metabolites, said immunopotentiating agent being isolated from the dialysis retentate.

9. The water soluble immunopotentiating agent produced according to the process of claim 8.

10. The process according to claim 1 wherein at least one of glucan-protein complex and a glucomannan-protein complex is sujected to extraction with from 10 to 100 times the amount by volume of a mixture of substantially equal amounts by volume of water and phenol and the aqueous phase is separated and thereafter dialyzed to remove any low molecular weight sugars, amino acids, peptides, lipids and yeast metabolites, said immunopotentiating agent being isolated from the dialysis retentate.

11. The water soluble immunopotentiating agent produced according to the process of claim 10.

* * * * *